United States Patent
Nagata et al.

(10) Patent No.: US 7,947,092 B1
(45) Date of Patent: May 24, 2011

(54) BATTERY WITH CATHODE HAVING INACTIVE MATERIALS

(75) Inventors: Mikito Nagata, Saugus, CA (US); Hisashi Tsukamoto, Santa Clarita, CA (US)

(73) Assignee: Quallion LLC, Sylmar, CA (US)

( * ) Notice: Subject to any disclaimer, the term of this patent is extended or adjusted under 35 U.S.C. 154(b) by 1266 days.

(21) Appl. No.: 11/389,444

(22) Filed: Mar. 23, 2006

(51) Int. Cl.
*H01M 10/38* (2006.01)

(52) U.S. Cl. .................. 29/623.5; 29/623.1; 429/231.1; 429/231.3

(58) Field of Classification Search .................. None
See application file for complete search history.

(56) References Cited

U.S. PATENT DOCUMENTS

| | | | | |
|---|---|---|---|---|
| 5,955,051 | A | * | 9/1999 | Li et al. ..................... 423/594.4 |
| 6,337,132 | B1 | * | 1/2002 | Kajiyama et al. ............. 428/403 |
| 7,381,496 | B2 | * | 6/2008 | Onnerud et al. ........... 429/231.1 |
| 2002/0110518 | A1 | * | 8/2002 | Okuda et al. .................. 423/594 |

* cited by examiner

*Primary Examiner* — John S Maples
(74) *Attorney, Agent, or Firm* — Gevnlovich, Dodd & Lindsey

(57) ABSTRACT

A battery includes an electrolyte activating one or more anodes and one or more cathodes. The electrolyte includes one or more salts in a solvent. One or more of the cathodes has a cathode medium that includes a lithium transition metal oxide as a cathode active material. The cathode medium also includes an inactive material that reacts with the electrolyte to form a passivation layer on the cathode medium. The passivation layer can include LiF. In some instances, the inactive material includes or consists of $Li_2CO_3$.

21 Claims, 7 Drawing Sheets

BATTERY WITH CATHODE HAVING INACTIVE MATERIALS

FIELD

The present invention relates to electrochemical devices, and more particularly to electrochemical devices having a cathode with one or more inactive materials.

BACKGROUND

The increased demand for lithium batteries has resulted in research and development to improve the capacity, rate and cycling performance of these batteries. These batteries often have an undesirably low calendar life and/or cycle life. Poor cycle life and/or calendar life may result from the cathode active material degrading during cycling and/or storage. For instance, the transition metal in a cathode active material can react with the electrolyte. As a result, there is a need for a battery having improved calendar life and/or cycle life.

SUMMARY

A battery includes an electrolyte activating one or more anodes and one or more cathodes. The electrolyte includes one or more salts in a solvent. One or more of the cathodes has a cathode medium that includes a lithium transition metal oxide as a cathode active material. The lithium transition metal oxide is coated with a layer of an inactive material that reacts with the electrolyte to form a passivation layer on the cathode medium. In some instances, the passivation layer resulting from the reaction between the electrolyte and the inactive material includes LiF. In some instances, the inactive material includes or consists of $Li_2CO_3$.

Another embodiment of the battery includes one or more cathodes. At least one of the cathodes has a cathode medium that includes a lithium transition metal oxide and $Li_2CO_3$. The battery also includes and an electrolyte activating the one or more cathodes and one or more anodes. The electrolyte includes one or more salts in a solvent.

A method of forming a battery includes generating a mixture that includes a lithium salt and a transition metal salt at a lithium:transition metal molar ratio between 1.01 and 1.09. The method also includes calcinating the mixture so as to generate a medium that includes a lithium transition metal oxide that serves as an active material in a cathode and a material that serves as an inactive material in a cathode. The method also includes generating the battery such that at least one cathode in the battery includes the medium. In some instances, the inactive material includes $Li_2CO_3$.

Another embodiment of a method of forming a battery includes generating a medium that includes a lithium transition metal oxide. The method also includes performing a test on the medium that indicates whether a material that serves as an inactive material in a cathode is present in the medium. The test includes a thermal gravimetric analysis of the medium. The method further includes using the medium in a battery cathode in response to the test indicating that the inactive material is present in the medium and excluding the medium in the battery cathode in response to the test indicating that the inactive material is not present in the medium.

DESCRIPTION

Figure 1:
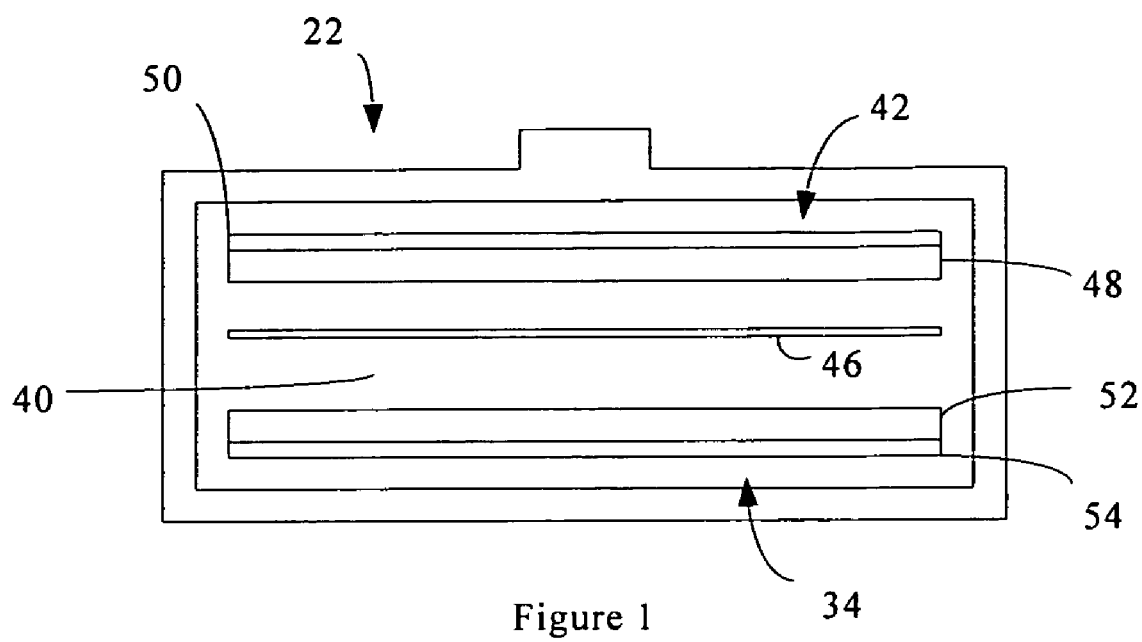
FIG. 1 is a schematic view of a battery.

A battery has an electrolyte activating one or more anodes and one or more cathodes. One or more of the cathodes include a cathode medium having an active material and an inactive material. The inactive material can be selected to react with the electrolyte so as to form a passivation layer that suppresses the reaction between the one or more active materials and the electrolyte. Suppressing the reaction between the one or more active materials and the electrolyte improves the cycling performance of the battery. For instance, a battery having a cathode that includes a lithium transition metal oxide as an active material and $Li_2CO_3$ as an inactive material has been generated. The $Li_2CO_3$ can react with a salt such as $LiPF_6$ in the electrolyte to form a LiF layer on the cathode. The LiF layer suppresses the reaction between the transition metal in the active material and the electrolyte and accordingly enhances the cycling performance of the battery. For instance, the inventors have achieved a cell having a discharge capacity retention higher than 85% at 800 cycles.

In some instances, a preliminary cathode medium is formed that includes the inactive material and the active material. The cathode medium is generated using the preliminary cathode medium. For instance, a slurry can be generated that includes the preliminary cathode medium in addition to other cathode medium components. The slurry can be coated on the cathode substrate and dried so as to form the cathode medium on the cathode substrate.

In some instances, the preliminary cathode medium is generated by calcinating a mixture of a lithium salt and a transition metal salt. When the molar ratio of the lithium:transition metal in the mixture is low, the calcination yields a preliminary cathode medium that includes lithium transition metal oxide without significant levels of inactive material. As the molar ratio increases, the calcination yields preliminary cathode medium that includes the lithium transition metal oxide and the inactive material. Without being bound to theory, the calcination process could result in a layer of the inactive material being coated on the particles of the active material. As a result, the cathode medium can include the inactive material coated on the active material. Coating the active material with the inactive material can ensure that the electrolyte contacts the inactive material. As a result, the passivation layer includes products of the reaction between the inactive material and the electrolyte.

In some instances, it may be desirable to test a batch of cathode medium and/or the preliminary cathode medium for the presence of the inactive material. For instance, when employing calcination to generate a preliminary cathode medium having low concentrations of the inactive material, it may be desirable to test the preliminary cathode medium for the presence of the inactive material. However, low concentrations of the inactive material may be desirable to prevent the inactive material from displacing enough active material to reduce the capacity and/or energy density of the battery. At low concentrations of inactive material, conventional methods such as x-ray diffraction analysis cannot indicate the presence of the inactive material. The inventors have found that even at low inactive material concentrations, thermo gravimetric analysis can indicate the presence of the inactive material in the cathode medium and/or the preliminary cathode medium. When the thermo gravimetric analysis indicates that inactive material is present in a batch of a preliminary cathode medium, inactive material from that batch can be employed in a cathode medium and when the thermo gravimetric analysis indicates that inactive material is absent from a batch of a preliminary cathode medium, inactive material from that batch can be excluded from the cathode medium.

FIG. 1 is a schematic view of a suitable battery 22. The battery 22 includes an electrolyte 40 activating a positive electrode or cathode 42 and a negative electrode or anode 34. A separator 46 is positioned between the cathode 42 and anode 34. The cathode 42 includes a cathode medium 48 on a cathode substrate 50. The anode 34 includes an anode medium 52 on an anode substrate 54. Although the battery is illustrated as including one anode and one cathode, the battery can include more than one anode and/or more than one cathode with the anodes and cathodes each separated by a separator. Additionally, the battery can have a variety of different configurations including, but not limited to, stacked configurations where multiple anodes and multiple cathodes are alternated in a stack, a "jellyroll" configurations, and wound configurations. In some instances, the battery is hermetically sealed. Hermetic sealing can reduce entry of impurities into the battery. As a result, hermetic sealing can reduce active material degradation reactions due to impurities. The reduction in impurity induced lithium consumption can stabilize battery capacity.

Suitable cathode substrates 50 include, but are not limited to, aluminum, stainless steel, titanium, or nickel substrates. The cathode medium 48 includes one or more cathode active materials. Suitable cathode active materials include, but are not limited to, lithium transition metal oxides. The lithium transition metal oxide can include elements in addition to lithium, one or more transition metals and oxygen or can consist of lithium, one or more transition metals and oxygen. In instances where the lithium transition metal oxide includes cobalt as a transition metal, the lithium transition metal oxide can include more than one transition metal. In some instances, the lithium transition metal oxide excludes cobalt. The transition metal in the lithium transition metal oxide can include or consist of one or more elements selected from the group consisting of Li, Al, Mg, Ti, B, Ga, Si, Mn, Zn, Mo, Nb, V, Ag, Ni, and Co. Suitable lithium transition metal oxides include, but are not limited to, $Li_xVO_y$, $LiCoO_2$, $LiNiO_2$, $LiNi_{1-x}Co_yMe_zO_2$, $LiMn_{0.5}Ni_{0.5}O_2$, $LiMn_{(1/3)}Co_{(1/3)}Ni_{(1/3)}O_2$, $LiFeO_2$, $Li_zM_{yy}O_4$, wherein Me is one or more transition metals such as Li, Al, Mg, Ti, B, Ga, Si, Mn, Zn, Mo, Nb, V, Ag and combinations thereof and M is one or more transition metals such as Mn, Ti, Ni, Co, Cu, Mg, Zn, V, and combinations thereof. In some instances, $0 < x < 1$ before initial charge of the battery and/or $0 < y < 1$ before initial charge of the battery and/or $x'$ is $\geq 0$ before initial charge of the battery and/or $1-x'+y'+z'=1$ and/or $0.8 < z < 1.5$ before initial charge of the battery and/or $1.5 < yy < 2.5$ before initial charge of the battery. Example lithium transition metal oxides include, but are not limited to, $LiCoO_2$, $LiNiO_2$, $LiNi_{1-x}Co_yMe_zO_2$, $LiMn_{0.5}Ni_{0.5}O_2$, $LiMn_{(1/3)}Co_{(1/3)}Ni_{(1/3)}O_2$, and $LiNiCo_yAl_zO_2$.

The cathode medium 48 includes one or more cathode inactive materials. Suitable inactive materials include, but are not limited to, inactive materials that include or consist of the elements lithium, and/or carbon, and/or oxygen. In some instances, the inactive materials exclude transition metals. Examples of suitable inactive materials include $Li(OH)$, $Li_2O$, and $Li_2CO_3$. An example of a suitable inactive material is $Li_2CO_3$. In some instances, one or more inactive materials are selected such that they preferentially react with the electrolyte over one of the active materials, more than one of the active materials or all of the active materials. The preference of the electrolyte for the inactive materials can ensure that the passivation layer includes contributions from the reaction between the inactive material and the electrolyte. The electrolyte preferentially reacts with an inactive material over an active material when the battery is filled with the electrolyte.

One or more of the active materials can be fully or partially coated with one or more inactive materials. The coating can be chemically bonded to one or more active materials, adhered to the one or more active materials and/or fused to the one or more active materials. Accordingly, a layer of the inactive material can be in direct contact with the one or more active materials. Further, additional materials may not be required to created adhesion between an inactive material and an active material. As a result, binder need not be positioned between the inactive material and the active material or need not bridge the inactive material and the active material and may only extend between active materials, inactive materials, and between an inactive material and an active material. When the cathode medium includes a plurality of active materials, the conducting medium on different active materials can be the same or different.

The molar ratio of the lithium in the active materials and inactive materials:transition metal in the active materials and inactive materials can be greater than 0.90, 0.98 and 1.02 and/or less than 1.18, 1.22 and 1.30. The ratio is preferably greater than 1.02 and less than 1.18. When an active material is coated with one or more inactive materials, the molar ratio of the lithium in that active material and those inactive materials:transition metal in that active materials and those inactive materials can be greater than 0.90, 0.98 and 1.02 and/or less than 1.18, 1.22 and 1.30.

The cathode medium 48 can optionally include binders, conductors and/or diluents such as PVDF, graphite and acetylene black in addition to the one or more cathode active materials. Suitable binders include, but are not limited to, PVdF, powdered fluoropolymer, powdered polytetrafluoroethylene or powdered polyvinylidene fluoride present at about 1 to about 5 weight percent of the cathode active material. Suitable conductors and/or diluents include, but are not limited to, acetylene black, carbon black and/or graphite or metallic powders such as powdered nickel, aluminum, titanium and stainless steel.

The cathode medium can optionally include carbon fibers that provide electrical pathways between the active materials in the cathode medium and/or between other components in the cathode medium. For instance, the carbon fibers can provide additional electrical pathways between the particles of the one or more coated active materials, between the particles of the one or more coated active materials and the cathode substrate, and/or between the particles of the one or more coated active materials and other components in the cathode medium.

Suitable carbon fibers for use in the cathode can have an average diameter of less than 5 μm. In some instances, the average diameter is 0.05 μm to 5 μm or 0.01 μm to 5 μm. The fibers can have agglomerations with an average size less than 500 μm where the size of an agglomeration is the longest dimension of the agglomeration. In some instances, the average agglomerate size is 5 μm to 500 μm. In a preferred example, none of the agglomerates are larger than 500 μm or smaller than 5 μm. The average fiber length can be less than 100 um and/or greater than 5 μm. Smaller fibers not provide electrical pathways sufficient to provide a long cycling life while longer fibers may penetrate the separator and cause internal shorts. An example of suitable carbon fibers is vapor grown carbon fiber (VGCF) and nanotubules.

When the cathode medium includes carbon fibers, the carbon fibers are preferably present in the cathode in an amount sufficient to provide electrical pathways between the cathode active materials. In some instances, the cathode is constructed such that the carbon fibers are less than 8 wt % of the cathode medium. Preferably, the carbon fibers are less than 6 wt % of the cathode medium, less than 5 wt % of the cathode medium. The carbon fibers can present in a range of 1 wt % to 6 wt % of the cathode medium or in a range of 2 wt % to 5 wt % of the cathode medium. Carbon fiber content less than 8 wt % can be preferred to allow the carbon fibers to provide electrical pathways between the active materials. As the wt % of the carbon fibers increases, the adhesive force provided by the binder can decrease because the high specific surface area begins to absorb the binder material so the binder material cannot serve as an adhesive in the positive electrode. The decreased adhesion is believed to reduce the number of available electric paths in the electrode and to accordingly degrade cycling performance.

To make a cathode, the cathode components are mixed together in a slurry. For instance, the active material, the inactive active material, the binder, carbon fiber, diluents and/or conductor are mixed together in a slurry. The slurry is applied to one or both sides of the cathode substrate, dried, and pressed or rolled to the desired thickness. The result can be cut to extract a cathode having the desired shape. In some instances, the cathode substrate is optional. For instance, the cathode medium can provide the functions of the both the cathode medium and the cathode substrate. As an example, the cathode medium can be formed into a pellet using a metal mesh for a current collector.

In some instances, the slurry is generated so as to include a preliminary cathode medium that includes or consists of one or more inactive materials and one or more active materials. In some instances, the preliminary cathode medium is generated by calcinating a mixture that includes or consists of one or more lithium salts and one or more transition metal salts. Suitable lithium salts for use in generating a preliminary cathode medium include, but are not limited to, $Li_2CO_3$, $LiOH.H_2O$, $LiNO_3$, and combinations thereof. Suitable transition metal salts for use in generating a preliminary cathode medium include, but are not limited to, $MNO_3$, $MOH$, and $MCO_3$, and combinations thereof where M is a transition metal.

When employing calcination to generate a preliminary cathode medium, the lithium salt and the transition metal salt should be well mixed before the calcination. Suitable methods for achieving a desirable degree of mixture include, but are not limited to, spray drying, co-precipitation, and sol-gel technologies. Spray drying includes dissolving the lithium salt and the transition metal salt in a solvent, mixing the resulting solution, and spraying the solution into an atmosphere that evaporates the solvent leaving mixed lithium salt and the transition metal salt.

When the molar ratio of the lithium:transition metal in the mixture of lithium salt and the transition metal salt is low, the calcination yields a preliminary cathode medium that includes lithium transition metal oxide without significant levels of inactive material. As the molar ratio increases, the calcination yields a preliminary cathode medium that includes lithium transition metal oxide and the inactive material. Experiments employing calcination to generate $Li_2CO_3$ as the inactive material and $LiNi_{0.8}Co_{0.15}Al_{0.05}O_2$ as the active material have shown that the preliminary cathode medium does not include significant levels of $Li_2CO_3$ until the molar ratio of the lithium:transition metal in the mixture of lithium salt and the transition metal salt, M, is greater than or equal to 1.02. Accordingly, the molar ratio of the lithium:transition metal in the mixture of lithium salt and the transition metal salt, M, can be greater than 1.02. When the molar ratio, M, exceeds 1.08, the $Li_2CO_3$ begins to displace the active material and the capacity and/or energy density of a battery employing the preliminary cathode medium begins to drop. Accordingly, the molar ratio of the lithium:transition metal in the mixture of lithium salt and the transition metal salt, M, can be less than 1.08. As a result, the molar ratio of the lithium:transition metal in the mixture of lithium salt and the transition metal salt, M, can be greater or equal than 1.02 and less than or equal to 1.08. Accordingly, when calcination is employed to generate a preliminary cathode medium having one or more active materials and one or more inactive materials, the molar ratio of the lithium:transition metal for those active materials and those inactive materials in the resulting cathode medium are greater than 0.90, 0.98 and 1.02 and/or less than 1.18, 1.22 and 1.30. The ratio is preferably greater than 1.02 and less than 1.18.

A batch of preliminary cathode material can be tested for the presence of the inactive material to determine whether the preliminary cathode material should be employed in a cathode medium. For instance, a thermo gravimetric analysis can be performed on a sample from the batch of the preliminary cathode material. A thermo gravimetric analysis measures the weight of a sample while scanning the temperature of an atmosphere in which the sample is placed. An example thermo gravimetric analysis can measure the weight of a sample while scanning the temperature of the atmosphere at a speed of 5° C./minute from 30° C. to 900° C. with an air flow of 200 ml/min. When the inactive material is present in the sample, the sample will show a weight drop at a temperature associated with decomposition of the inactive material in the sample. Accordingly, the thermo gravimetric analysis indicates that the inactive material is present in the preliminary cathode medium when a weight drop occurs at the associated temperature and the thermo gravimetric analysis indicates that the inactive material is absent from the preliminary cathode medium when the weight drop fails to occur at the associated temperature. When the thermo gravimetric analysis indicates that inactive material is present in a batch of a preliminary cathode medium, inactive material from that batch can be employed in a cathode medium and when the thermo gravimetric analysis indicates that inactive material is absent from a batch of a preliminary cathode medium, inactive material from that batch can be excluded from the cathode medium. When a batch of preliminary inactive material is excluded from the cathode medium, the batch of preliminary inactive material can be discarded or can be further processed before generating a cathode medium that includes that preliminary inactive material. For instance, additional inactive material can be added to the preliminary inactive material and then a cathode medium can be generated using the preliminary inactive material with the additional inactive material.

In addition or as an alternative to using thermo gravimetric analysis to test for the presence of the inactive material in a preliminary cathode material, thermo gravimetric analysis can be employed to determined whether the preliminary cathode material has the desired molar ratio of lithium:transition metal. For instance, a relationship can be experimentally determined between the percentage of weight loss to the preliminary cathode material in a particular temperature range and the ratio of lithium:transition metal. As a result, the percentage of weight loss to the preliminary cathode material in a particular temperature range can be compared to the relationship to approximate the molar ratio of lithium:transition metal in the sample of the preliminary cathode material. When the thermo gravimetric analysis on the sample indicates that a batch of a preliminary cathode medium has the desired molar ratio of lithium:transition metal, inactive material from that batch can be employed in a cathode medium. When the thermo gravimetric analysis on the sample indicates that a batch of a preliminary cathode medium does not have the desired molar ratio of lithium:transition metal, inactive material from that batch can be excluded from the cathode medium. When a batch of preliminary inactive material is excluded from the cathode medium, the batch of preliminary inactive material can be discarded or can be further processed before generating a cathode medium that includes that preliminary inactive material. For instance, additional inactive material can be added to the preliminary inactive material and then a cathode medium can be generated using the preliminary inactive material with the additional inactive material.

When calcination is employed to generate a preliminary cathode medium that includes an inactive material, a layer of the inactive material may be coated on the particles of the active material. Accordingly, the use of calcination to generate the preliminary cathode medium could yield a preliminary cathode medium having one or more active materials coated with a layer of one or more inactive materials.

Suitable anode substrates 54 include, but are not limited to, lithium metal, titanium, a titanium alloy, stainless steel, nickel, copper, tungsten, tantalum and alloys thereof.

The anode medium 52 includes or consists of one or more anode active materials. The anode active material can include or consist of a metal selected from Groups IA, IIA, IIIB and IVB of the Periodic Table of the Elements. Examples of these anode active materials include lithium, sodium, potassium and their alloys and intermetallic compounds. Examples of suitable alloys include, but are not limited to, Li—Si, Li—Al, Li—B, Li—Si—B. Another example of a suitable lithium alloy is a lithium-aluminum alloy. However, increasing the amounts of aluminum present in the alloy can reduce the energy density of the cell. Examples of suitable intermetallic compounds include, but are not limited to, intermetallic compounds that include or consist of two or more components selected from the group consisting of Li, Ti, Cu, Sb, Mn, Al, Si, Pb, Sn, In, Bi, Ag, Ba, Ca, Hg, Pd, Pt, Te, Zn and La. Other examples of suitable intermetallic compounds include, but are not limited to, intermetallic compounds that include or consist of lithium metal and one or more components selected from the group consisting of Ti, Cu, Sb, Mn, Al, Si, Pb, Sn, In, Bi, Ag, Ba, Ca, Hg, Pd, Pt, Te, Zn and La. Specific example of intermetallic compounds include $Cu_6Sn_5$, $Cu_2Sb$, MnSb. Other suitable anode active materials include lithium titanium oxides such as $Li_4Ti_5O_{12}$, silica alloys and mixtures of the above anode active materials. Another example of a suitable anode active material includes or consists of a carbonaceous mixture. For instance, the carbonaceous mixture can include a mixture that includes or consists of one, two or three components selected from the group consisting of: amorphous carbon, carbon beads, carbon fibers, graphite flakes, and graphite spheres.

Another example of a suitable anode active material includes or consists of a carbonaceous mixture. For instance, the carbonaceous mixture can include a mixture that includes or consists of one, two or three components selected from the group consisting of: carbon beads, carbon fibers, and graphite flakes.

The carbon beads can have shapes that approximate blocks, spheres, spheroids, cylinders, cubes or combinations of these shapes. In some instances, the carbon beads have a real density of greater than 2.2 g/cc; a surface area of less than 3 $m^2/g$ or less than 2 $m^2/g$, or less than 1 $m^2/g$ as measured by BET where BET is the analytical method employed to measure the specific surface area of powder based on the BET adsorption isotherm reported by Brunauer, Emmert, and Teller; and/or an average particle size of less than 40 μm and/or in a range of 5-35 μm. In some instances, the carbon beads may have a structure that is inherently rigid. Alternatively or additionally, the carbon beads may have a rigid surface layer that makes them difficult to deform. For instance, the carbon beads can have a rigid surface layer that includes hard carbon. The carbon beads can provide structural support to the anode medium 52 of the present invention. The structural support can help maintain the porosity of the anode medium 52. The porosity of the anode medium 52 can enhance the contact between the electrolyte and the carbon. Additionally, the bead shape can help minimize the surface area of the graphite within the carbonaceous mixture. As a result, the carbon beads can limit the amount of lithium required to form a passivation layer, or solid electrolyte interface (SEI) on the anode. Carbon beads generally have fewer side reactions such as electrolyte decomposition relative to other shapes of carbon materials. The carbon beads may be mesocarbon microbeads produced by subjecting mesophase spherules, produced during the carbonization of pitch, to heat treatment for graphitization. An example of the carbon beads is mesocarbon microbeads (MCMB) which are available from Osaka Gas Chemicals Co., LTD.

In some instances, the carbon fibers have a specific surface area of less than 5 $m^2/g$; an average particle size of less than 40 μm and/or in a range of 5-35 μm; a d002 (layer distance) of less than 3.36 Å; and an Lc of greater than 100 nm. Carbon fibers that are too long may cause microshorts by penetrating the separator 46. The carbon fibers can improve packing density and conductivity. Carbon fibers can also intensify the stiffness of the anode and reduce swelling and decomposition of the anode. The carbon fibers may be a vapor grown carbon fiber. The carbon fiber may be prepared by subjecting hydrocarbons such as benzene, methane, propane, and so on to vapor phase heat-decomposition under the presence of catalyst base plate made of Fe, Ni, Co, and so on in order to make carbon fibers deposit and grow on the base plate. Other examples are pitch carbon fibers, made from petroleum or coal pitch as a raw material through a spinning and carbonating treatment, and carbon fibers made from polyacrylonitrile (PAN), which may be used in the invention.

The graphite flakes can be natural or artificial graphite flakes. The graphite flakes can be softer than carbon beads. The flakes tend to reduce friction in the carbon mixture because the planes of carbon can slip with respect to one another, allowing the graphite flakes to fit within the spaces in the mixture. In some instances, the graphite flakes are less than 40 μm or in a range 5-35 μm.

When the anode active material includes carbon beads, the carbon fibers, and the graphite flakes, the anode medium 52 can have a porosity of 25-45%, and the cathode medium 48 can have a porosity of 20-40%.

An example embodiment of the anode active material includes or consists of carbon beads and carbon fibers. A further example embodiment of the anode active material includes carbon beads and carbon fibers and excludes carbon flakes. Another example embodiment of the anode active material includes or consists of carbon beads, carbon fibers, and graphite flakes. In another example, the anode active material includes carbon beads, carbon fibers, and graphite flakes with an average particle size of less than 40 μm, in a ratio of approximately 70% carbon beads:22.5% carbon fibers:7.5% graphite flakes. Additional description of anodes constructed with a carbonaceous mixture are provided in U.S. patent application Ser. No. 10/264,870, filed on Oct. 3, 2002, entitled "Negative Electrode for a Nonaqueous Battery," and incorporated herein in its entirety, which claims priority to U.S. Provisional Patent Application Ser. No. 60/406,846, filed on Aug. 29, 2002, and entitled "Negative Electrode for a Nonaqueous Battery," and incorporated herein in its entirety.

Suitable binders for use with the anode medium include, but are not limited to, PVdF. When the anode active material includes a carbonaceous mixture, the binder of the anode medium can exclude fluorine, and can include carboxymethyl cellulose (CMC). Styrene butadiene rubber (SBR) can be added to impart elasticity to the mixture. As an alternative to a binder that consists of CMC and SBR, a different fluorine excluding binder or a fluorine-containing binder may be used. A dispersion in water of the carbonaceous mixture, CMC, and SBR can be made to form a slurry that can be coated onto to a metal foil substrate.

In some instances, the anode consists of the anode medium. Accordingly, the anode medium also serves as the anode substrate. For instance, the anode can consist of lithium metal.

The anode can be generated by generating a slurry that includes or consists of the components of the anode medium. The slurry can be coated onto a substrate, dried and pressed to the desired thickness. The result can be cut to extract an anode having the desired shape.

Additional anode constructions are provided in U.S. patent application Ser. No. 11/759,879, filed on Jul. 5, 2005, entitled "Battery Having Negative Electrode Including Amorphous Carbon;" and is a continuation-in-part of U.S. patent application Ser. No. 11/284,861, filed Nov. 22, 2005, entitled "Battery Having Negative Electrode Including Amorphous Carbon."

Suitable separators 46 include, but are not limited to, polyolefins such as polyethylene. Illustrative separator materials also include fabrics woven from fluoropolymeric fibers including polyvinylidine fluoride, polyethylenetetrafluoroethylene, and polyethylenechlorotrifluoroethylene used either alone or laminated with a fluoropolymeric microporous film, non-woven glass, polypropylene, polyethylene, glass fiber materials, ceramics, polytetrafluoroethylene membrane commercially available under the designation ZITEX (Chemplast Inc.), polypropylene/polyethylene membrane commercially available under the designation CELGARD (Celanese Plastic Company, Inc.), a membrane commercially available under the designation DEXIGLAS (C.H. Dexter, Div., Dexter Corp.), and a polyethylene membrane commercially available from Tonen Chemical Corp.

The electrolyte includes one or more salts in a solvent. The electrolyte can be prepared such that the total concentration of the one or more salts in the solvent is about 0.3 to 2.0 M, about 0.5 to 1.5 M, or about 0.7 to 1.2 M. Suitable salts for use with the electrolyte include, but are not limited to, alkali metal salts including lithium salts. Examples of lithium salts include $LiClO_4$, $LiBF_4$, $LiAsF_6$, $LiPF_6$, $LiSbF_6$, $LiCF_3SO_3$, $LiC_6F_5SO_3$, $LiC(CF_3SO_2)_3$, $LiN(SO_2C_2F_5)_2$, $LiN(SO_2CF_3)_2$, (LiTFSI), $LiAlCl_4$, $LiGaCl_4$, LiSCN, $LiO_2$, $LiO_3SCF_3$, $LiO_2CCF_3$, $LiSO_6F$, $LiB(C_6H_5)_4$, $LiB_{10}C_{10}$, Li-methide, Li-imide, lithium alkyl fluorophosphates and combinations thereof. Preferred salts include $LiPF_6$ and $LiBF_4$.

In addition to the above salts or as an alternative to the above salts, the electrolyte can include one or more organoborate salts. Suitable organoborate salts include aromatic lithium bis[bidentate]borates, also known as a bis[chelato] borate, such as bis[benzenediolato (2–)-O,O']borate, bis[substituted benzenediolato (2–)-O,O']borate, bis[salicylato]borate, bis[substituted salicylato]borate, bis[2,2'-biphenyldiolato(O,O')]borate, and bis[substituted 2,2'-biphenyldiolato (O,O')]borate]. In some instances, the organoborate salt is a nonaromatic bis[chelato]borate, such as bis[oxalato (2–)-O,O']borate, bis[malonato (2–)-O,O']borate, bis[succinato]borate, [.alpha.-hydroxy-carboxylato]borate, [.alpha.-hydroxy-carboxylato]borate, [.beta.-hydroxy-carboxylato]borate, [.beta.-hydroxy-carboxylato]borate, [.alpha.-dicarboxylato]borate, and [.alpha.-dicarboxylato] borate. In some instances, the organoborate salt is a mono [bidentate]borate, a tridentate borate, or a tetradentate borate. Examples of suitable organoborate salt include lithium bis (tetrafluoroethylenediolato)borate $LiB(OCF_2CF_2O)_2$, lithium bis(hexafluoropropylenediolato)borate LiB[OCF $(CF_3)CF_2O]_2$ and lithium bis[1,2-tetrakis(trifluoromethyl) ethylenedialato(2–)O,O-']borate or lithium bis(perfluoropinacolato)borate $LiB[OC(CF_3)_2C(CF_3)_2O]_2$ or $LiB[OC (CF_3)_2]_4$. Preferred lithium organoborate salts are lithium bis-oxalato borate (LiBOB), and lithium difluoro oxalato borate (LiDfOB).

Examples of suitable organoborate salts are disclosed in U.S. Patent Application Ser. No. 60/565,211, filed on Apr. 22, 2004, entitled "Organoborate Salt in Electrochemical Device Electrolytes" and incorporated herein in its entirety.

The solvent can include or consist of one or more organic solvents. Suitable organic solvents include, but are not limited to, carbonates, ethers, esters, amides, polyalkylene oxides, polycarbonates, polyesters, polyamides and combinations thereof. Examples of suitable solvents include, but are not limited to, cyclic carbonates such as propylene carbonate (PC), ethylene carbonate (EC), butylene carbonate (BC) and vinylene carbonate (VC), linear carbonates such as dimethyl carbonate (DMC), diethyl carbonate (DEC), ethylmethyl carbonate (EMC) and dipropyl carbonate (DPC), dialkyl carbonates such as diglyme, trigylme, tetragylme, 1,2-dimethoxyethane (DME), methyl propyl carbonate, ethyl propyl carbonate, esters, aliphatic carboxylate esters such as methyl formate, methyl acetate and ethyl propionate, gamma.-lactones such as .gamma.-butyrolactone, linear ethers such as 1,2-ethoxyethane (DEE) and ethoxymethoxyethane (EME), cyclic ethers such as tetrahydrofuran and 2-methyltetrahydrofuran, and aprotic organic solvents such as dimethylsulfoxide, 1,3-dioxolane, formamide, acetoamide, dimethylformamide, dioxolane, acetonitrile, propylnitrile, nitromethane, ethylmonoglyme, triester phosphate, timethoxymethane, dioxolane-derivatives, sulphorane, methylsulphorane, 1,3-diemthyl-2-imidazoline, 3-methyl-2-oxazolidinone, propylene carbonate-derivatives, tetrahydrofuran-derivatives, ethylether, 1,3-propanesultone, anisole, N-methylpyrrolidone and fluorinated carboxylate esters. In some instances, the solvent excludes organic solvents.

In addition to the one or more organic solvents, the solvent can include one or more silanes and one or more siloxanes. Suitable siloxanes include polysiloxanes, tetrasiloxanes, trisiloxanes, disiloxanes and combinations thereof. Examples of suitable polysiloxane electrolytes are disclosed in U.S. patent application Ser. No. 10/810,019, filed on Mar. 25, 2004, entitled "Polysiloxane for Use in Electrochemical Cells," and incorporated herein in its entirety. Examples of suitable tetrasiloxane and tetrasiloxane electrolytes are disclosed in U.S. Provisional Patent Application Ser. No. 60/543,951, filed on Feb. 11, 2004, entitled "Siloxanes;" and in U.S. patent application Ser. No. 10/971,926, filed on Oct. 21, 2004, and entitled "Electrochemical Device Having Electrolyte Including Tetrasiloxane;" and in U.S. patent application Ser. No. 11/056,868, filed on Feb. 10, 2005, and entitled "Electrochemical Device Having Electrolyte Including Tetrasiloxane;" each of which is incorporated herein in its entirety. Examples of suitable trisiloxanes and trisiloxane electrolytes are disclosed in U.S. Provisional Patent Application Ser. No. 60/543,951, filed on Feb. 11, 2004, entitled "Siloxanes;" and U.S. Provisional Patent Application Ser. No. 60/542,017, filed on Feb. 4, 2004, entitled "Nonaqueous Electrolyte Solvents for Electrochemical Devices;" and U.S. Provisional Patent Application Ser. No. 60/543,898, filed on Feb. 11, 2004, entitled "Siloxane Based Electrolytes for Use in Electrochemical Devices;" and in U.S. patent application Ser. No. 10/971,913, filed on Oct. 21, 2004, and entitled "Electrochemical Device Having Electrolyte Including Trisiloxane;" and in U.S. patent application Ser. No. 11/056,867, filed on Feb. 10, 2005, and entitled "Electrochemical Device Having Electrolyte Including Trisiloxane;" each of which is incorporated herein in its entirety. Examples of suitable disiloxanes and disiloxane electrolytes are disclosed in U.S. Provisional Patent Application Ser. No. 60/543,951, filed on Feb. 11, 2004, entitled "Siloxanes;" and U.S. Provisional Patent Application Ser. No. 60/542,017, filed on Feb. 4, 2004, entitled "Nonaqueous Electrolyte Solvents for Electrochemical Devices;" and U.S. Provisional Patent Application Ser. No. 60/543,898, filed on Feb. 11, 2004, entitled "Siloxane Based Electrolytes for Use in Electrochemical Devices," and in U.S. patent application Ser. No. 10/971,507, filed on Oct. 21, 2004, and entitled "Electrochemical Device Having Electrolyte Including Disiloxane;" and in U.S. patent application Ser. No. 11/056,869, filed on Feb. 10, 2005, and entitled "Electrochemical Device Having Electrolyte Including Disiloxane;" each of which is incorporated herein in its entirety. Examples of suitable silanes and silane electrolytes are disclosed in U.S. Provisional Patent Application Ser. No. 60/601,452, filed on Aug. 13, 2004, entitled "Electrolyte Including Silane for Use in Electrochemical Devices;" and in U.S. patent application Ser. No. 10/977,313, filed on Oct. 28, 2004, and entitled "Electrolyte Including Silane for Use in Electrochemical Device;" and in U.S. patent application Ser. No. 11/056,869, filed on Feb. 10, 2005, and entitled "Electrolyte Including Silane for Use in Electrochemical Device;" each of which is incorporated herein in its entirety.

In some instances, the solvent includes one or more organic solvents in addition to one or more of the silanes and/or one or more of the siloxanes. Organic solvents can reduce the viscosity of the siloxanes and/or the silanes. When the solvent includes one or more organic solvents in addition to one or more siloxanes and/or one or more silanes, a suitable volume ratio of the total organic solvents to the total siloxane and silane is greater than 1:99, 1:9, or 3:7 and/or less than 9:1, 4:1 or 7:3. The solvent can include more than one of the siloxane or more than one silane. Further, the solvent can include one or more siloxanes combined with one or more silanes. The combination of a silane with other silanes and/or with other siloxanes can reduce the viscosity of the blended solvent. Additionally, the inventors believe that the silanes can improve the mobility of poly(alkylene oxide) in other siloxanes or silanes. Additionally, the combination of a silane with other silanes and/or siloxanes can increase the ability of the solvent to dissociate the salts employed in electrolyte and can accordingly increase the concentration of free ions in the electrolyte. These features can further enhance the ionic conductivity of the electrolytes.

The solvent can include one or more passivation additives that form a passivation layer on the anode and/or on the cathode. In some instances, the passivation additive is reduced and polymerizes at the surface of the anode to form the passivation layer. Vinyl carbonate (VC) and vinyl ethylene carbonate (VEC) are examples of additives that can form a passivation layer by being reduced and polymerizing to form a passivation layer. The result of the reduction in the presence of lithium is $Li_2CO_3$ and butadiene that polymerizes in the presence of an available electron at the anode surface. Ethylene sulfite (ES) and propylene sulfite (PS) form passivation layers by mechanisms that are similar to VC and VEC. In some instances, one or more of the passivation additives has a reduction potential that exceeds the reduction potential of the components in the solvent. For instance, VEC and VC have a reduction potential of about 2.3V. This arrangement of reduction potentials can encourage the passivation additive to form the passivation layer before reduction of other electrolyte components and can accordingly reduce consumption of other electrolyte components.

Suitable passivation additives include, but are not limited to, carbonates having one or more unsaturated substituents. For instance, suitable passivation additives include unsaturated and unsubstituted cyclic carbonates such as vinyl carbonate (VC); cyclic alkylene carbonates having one or more unsaturated substituents such as vinyl ethylene carbonate (VEC), and o-phenylene carbonate (CC, $C_7H_4O_3$); cyclic alkylene carbonates having one or more halogenated alkyl substituents such as ethylene carbonate substituted with a trifluormethyl group (trifluoropropylene carbonate, TFPC); linear carbonates having one or more unsaturated substituents such as ethyl 2-propenyl ethyl carbonate ($C_2H_5CO_3C_3H_5$); saturated or unsaturated halogenated cyclic alkylene carbonates such as fluoroethylene carbonate (FEC) and chloroethylene carbonate (ClEC). Other suitable passivation additives include, acetates having one or more unsaturated substituents such as vinyl acetate (VA). Other suitable passivation additives include cyclic alkyl sulfites and linear sulfites. For instance, suitable passivation additives include unsubstituted cyclic alkyl sulfites such as ethylene sulfite (ES); substituted cyclic alkylene sulfites such as ethylene sulfite substituted with an alkyl group such as a methyl group (propylene sulfite, PS); linear sulfites having one or more one more alkyl substituents and dialkyl sulfites such as dimethyl sulfite (DMS) and diethyl sulfite (DES). Other suitable passivation additives include halogenated-gamma-butyrolactones such as bromo-gamma-butyrolactone (BrGBL) and fluoro-gamma-butyrolactone (FGBL).

The passivation additives can include or consist of one or more passivation additives selected from the group consisting of: dimethyl sulfite (DMS), diethyl sulfite (DES), bromo-gamma-butyrolactone (BrGBL), fluoro-gamma-butyrolactone (FGBL), vinyl carbonate (VC), vinyl ethylene carbonate (VEC), ethylene sulfite (ES), CC, trifluoropropylene carbonate (TFPC), 2-propenyl ethyl carbonate, fluoroethylene carbonate (FEC), chloroethylene carbonate (ClEC), vinyl acetate (VA), propylene sulfite (PS), 1,3 dimethyl butadiene, styrene carbonate, phenyl ethylene carbonate (PhEC), aromatic carbonates, vinyl pyrrole, vinyl piperazine, vinyl piperidine, vinyl pyridine, and mixtures thereof. In another example, the electrolyte includes or consists of one or more passivation additives selected from the group consisting of vinyl carbonate (VC), vinyl ethylene carbonate (VEC), ethylene sulfite (ES), propylene sulfite (PS), and phenyl ethylene carbonate (PhEC). In a preferred example, the electrolyte includes or consists of one or more passivation additives selected from the group consisting of vinyl carbonate (VC), vinyl ethylene carbonate (VEC), ethylene sulfite (ES), and propylene sulfite (PS). In another preferred example, the electrolyte includes vinyl carbonate (VC) and/or vinyl ethylene carbonate (VEC).

In some conditions, certain organoborate salts, such as LiDfOB, can form a passivation layer. As a result, the desirability and/or concentration of passivation additives may be reduced when organoborate are employed as salts.

In some instances, the concentration of passivation additives in the electrolyte does not greatly exceed the concentration needed to form the passivation layer. An excess concentration of the passivation additive can produce an excessively thick passivation layer that increases the internal resistance of the battery and/or increase voltage delay. Additionally, it is currently believed that excess amounts of certain passivation additives, such as organoborate salts, in the electrolyte can reduce the electrolyte conductivity. Suitable concentration for a particular passivation additive before discharge of the battery in the electrolyte includes, but is not limited to, concentrations greater than 0.005, greater than 0.001 M and/or less than 0.05 M, less than 0.2 M or less than 1.5 M. In a preferred embodiment, before discharge of the battery at least one passivation additive is present in the electrolyte at a concentration of less than 0.1 M. A suitable concentration for the total amount of passivation additive in the electrolyte before discharge of the battery includes, but is not limited to, concentrations greater than 0.005, greater than 0.001 M and/or less than 0.05 M, less than 0.2 M or less than 1.5 M. In some instances, the total concentration of the passivation additive in the solvent includes, but is not limited to, concentrations greater than 0.1 wt %, greater than 0.5 wt % and/or less than 5 wt %, less than 20 wt %, or less than 35 wt %. In a preferred embodiment, the concentration of the additive is less than 3 wt % or less than 2 wt % of the solvent.

When the electrolyte includes an organoborate salt that forms a passivation layer, the total concentration of the organoborate salts in the electrolyte before discharge of the battery can be smaller than the total concentration of the one or more non-organoborate salts. Before discharge of the battery or before formation of the passivation layer, a suitable molar ratio of the total concentration of the non-organoborate salts: total organoborate concentration ratios greater than 4:1, 10:1, 40:1, or 200:1 and/or less than 50:1, 100:1, 400:1 or 800:1. In some instances, the molar ratio is in a range of 50:1 to 200:1. The concentration of the one or more organoborate salts may drop after formation of the passivation layer because the one or more organoborate salts may be consumed during formation of the passivation layer. In some instances, the concentration of the organoborate salt(s) that form the passivation layer on anode and/or cathode substantially exceeds the concentration needed to form the passivation layer.

The electrolyte can be a liquid. In some instances, the electrolyte is a solid or a gel. For instance, the electrolyte can include a network polymer that interacts with the solvent to form an interpenetrating network. The interpenetrating network can serve as a mechanism for providing a solid electrolyte or gel electrolyte. Alternately, the electrolyte can include one or more solid polymers that are each a solid at room temperature when standing alone. The solid polymer can be employed in conjunction with the solvent to generate an electrolyte such as a plasticized electrolyte as a solid or as a gel. Alternately, one or more silanes and/or one or more siloxanes in the solvent can be cross linked to provide a solid or gel electrolyte. A polysiloxane is an example of a cross-linkable solvent. Suitable examples for method of forming a cross linked polymer are disclosed in U.S. patent application Ser. No. 10/810,019, filed on Mar. 25, 2004, entitled "Polysiloxane for Use in Electrochemical Cells" and incorporated herein in its entirety.

The electrolyte can be generated by combining the one or more salts and the solvent. In some instances, other components are combined with the solvent. For instance, the monomers for an interpenetrating network can also be combined with the solvent. A suitable concentration for the salt in the electrolyte is a concentration greater than 0.1 M, 0.5 M or greater than 0.7 M and/or less than 1.5 M, less than 2 M, or less than 5 M. For instance, the electrolyte can include 0.8 M to 1.5 M $LiAsF_6$ or $LiPF_6$ in a 50:50 mixture, by volume, of propylene carbonate and 1,2-dimethoxyethane. Another example of the electrolyte includes electrolyte 1.2 M $LiBF_4$ in a 30:70 by volume mixture of PC and DME.

The battery can be a primary battery or a secondary battery. Further, the above cathode, anode and electrolyte combinations can be employed in other electrochemical devices such as capacitors and hybrid capacitors/batteries.

EXAMPLE 1

A first preliminary cathode medium was generated. A mixture of Li(OH) and $Ni_{0.8}Co_{0.15}Al_{0.05}(OH)_x(NO_3)_y$ was generated with x=0.86 and y=0.14 and a lithium to transition metal molar ratio of about 1.02:1.00. The mixture was generated by the spray dry method where the Li(OH) and $Ni_{0.8}Co_{0.15}Al_{0.05}(OH)_x(NO_3)_y$ were dissolved in water and sprayed into heated air to evaporate the water. The mixture was calcinated in an oxygen atmosphere at about 720° C. so as to provide a first preliminary cathode medium that includes $LiNi_{0.8}Co_{0.15}Al_{0.05}O_2$.

A second preliminary cathode medium was generated. A mixture of Li(OH) and $Ni_{0.8}Co_{0.15}Al_{0.05}(OH)_x(NO_3)_y$ was generated with x=0.86 and y=0.14 and a lithium to transition metal molar ratio of about 1.05:1.00. The mixture was generated by the spray dry method where the Li(OH) and $Ni_{0.8}Co_{0.15}Al_{0.05}(OH)_x(NO_3)_y$ were dissolved in water and sprayed into heated air to evaporate the water. The mixture was calcinated in an oxygen atmosphere at about 720° C. so as to provide the second preliminary cathode medium that includes $LiNi_{0.8}Co_{0.15}Al_{0.50}O_2$.

Figure 2A:
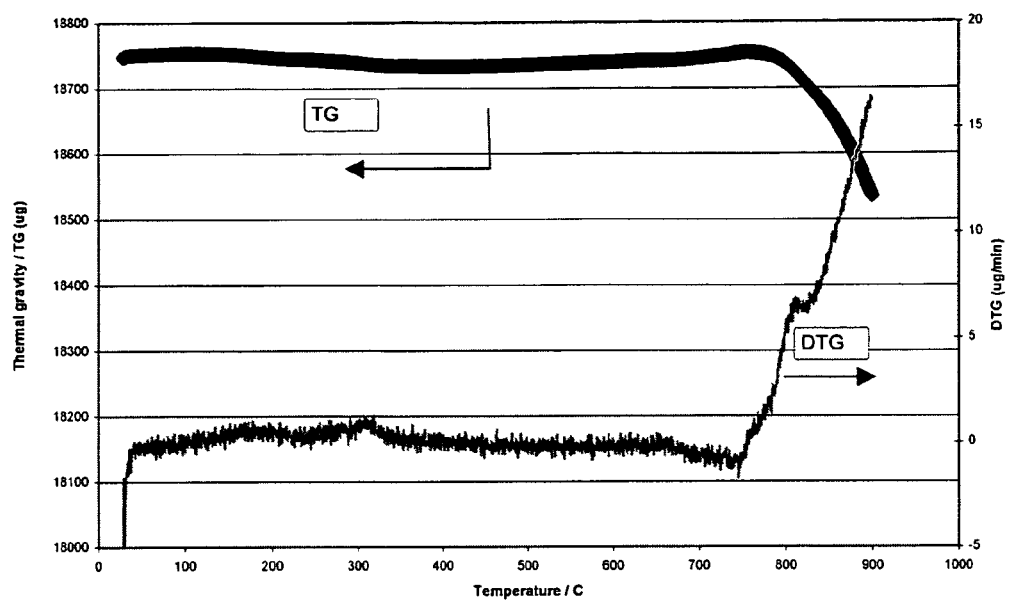
FIG. 2A illustrates the results of a thermo gravimetric analysis on a medium generated from calcination of a mixture of Li(OH) and $Ni_{0.8}Co_{0.15}Al_{0.15}(OH)_x(NO_3)_y$, with x=0.86, y=0.14 and a lithium to transition metal molar ratio of about 1.02:1.00.
Figure 2B:
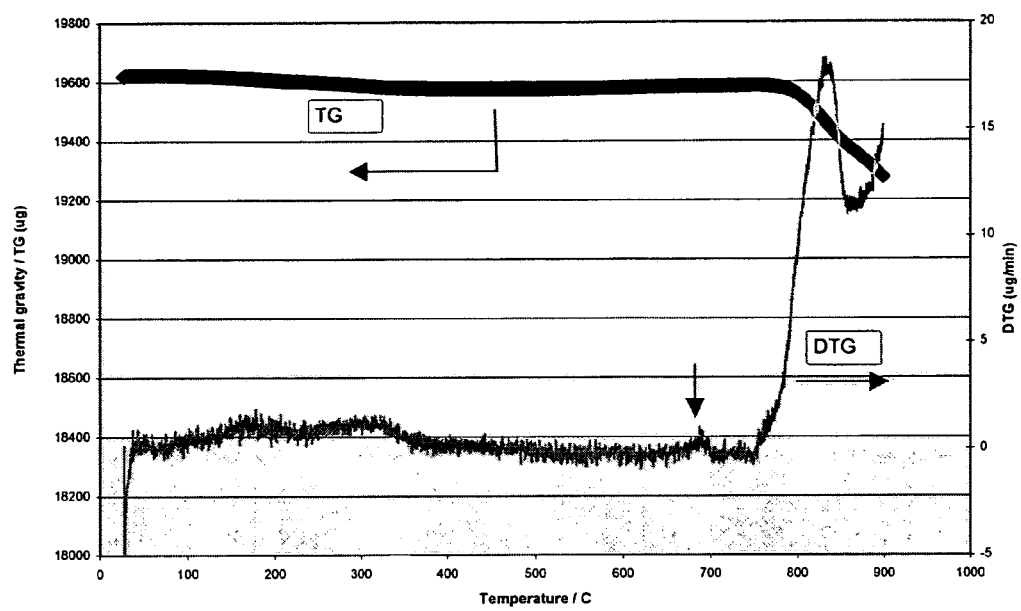
FIG. 2B illustrates the results of a thermo gravimetric analysis on a medium generated from calcination of a mixture of Li(OH) and $Ni_{0.8}Co_{0.15}Al_{0.05}(OH)_x(NO_3)_y$, with x=0.86, y=0.16 and a lithium to transition metal molar ratio of about 1.05:1.00.

A first thermo gravimetric analysis was performed on the first preliminary cathode medium. A second thermo gravimetric analysis was performed on the second preliminary cathode medium. A third thermo gravimetric analysis was performed on a sample of $Li_2CO_3$. The thermo gravimetric analysis was performed using a Perkin Elmer TG/TDA 6300 at a scan speed of 5° C./minute from 30° C. to 900° C. with an air flow of 200 ml/min. The results of the first thermo gravimetric analysis are presented in FIG. 2A. The results of the second thermo gravimetric analysis are presented in FIG. 2B. The results of the third thermo gravimetric analysis are presented in FIG. 2C.

Figure 2C:
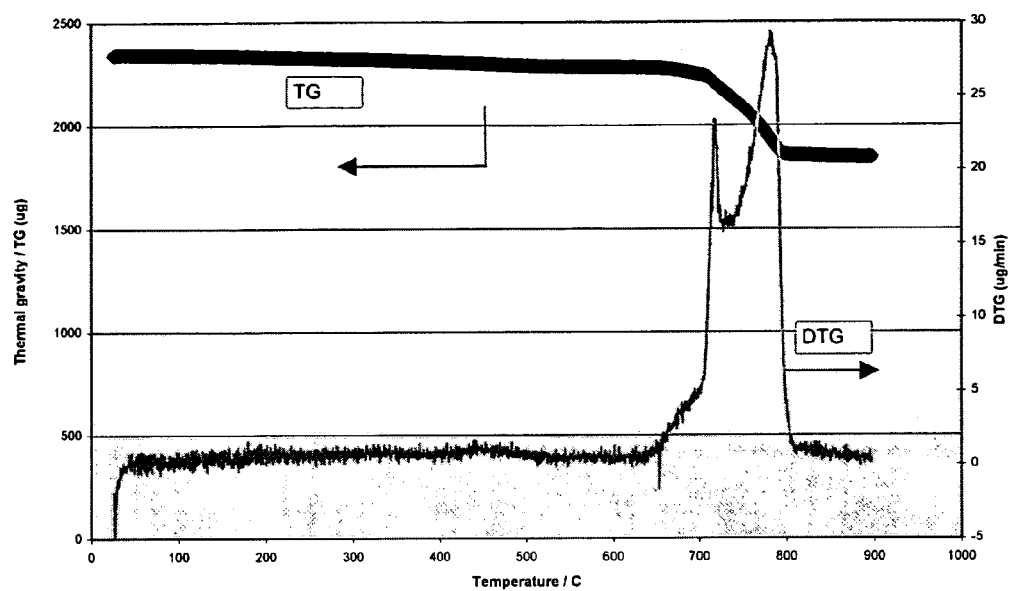
FIG. 2C illustrates the results of a thermo gravimetric analysis on $Li_2CO_3$.

As evidenced by FIG. 2C, decomposition of the $Li_2CO_3$ occurs between 650° C. and 700° C. As evidenced by the absence of a weight drop between 650° C. and 800° C. in FIG. 2A, the first preliminary cathode medium does not show the decomposition associated with the presence of $Li_2CO_3$. However, the second preliminary cathode medium shows the decomposition associated with the presence of $Li_2CO_3$ as best seen from the dTG curve between 650° C. and 700° C. in FIG. 2B. These results indicate that a lithium to transition metal molar ratio of greater than about 1.02:1.00 provides a preliminary cathode medium having $Li_2CO_3$ and a lithium transition metal oxide.

EXAMPLE 2

Figure 3:
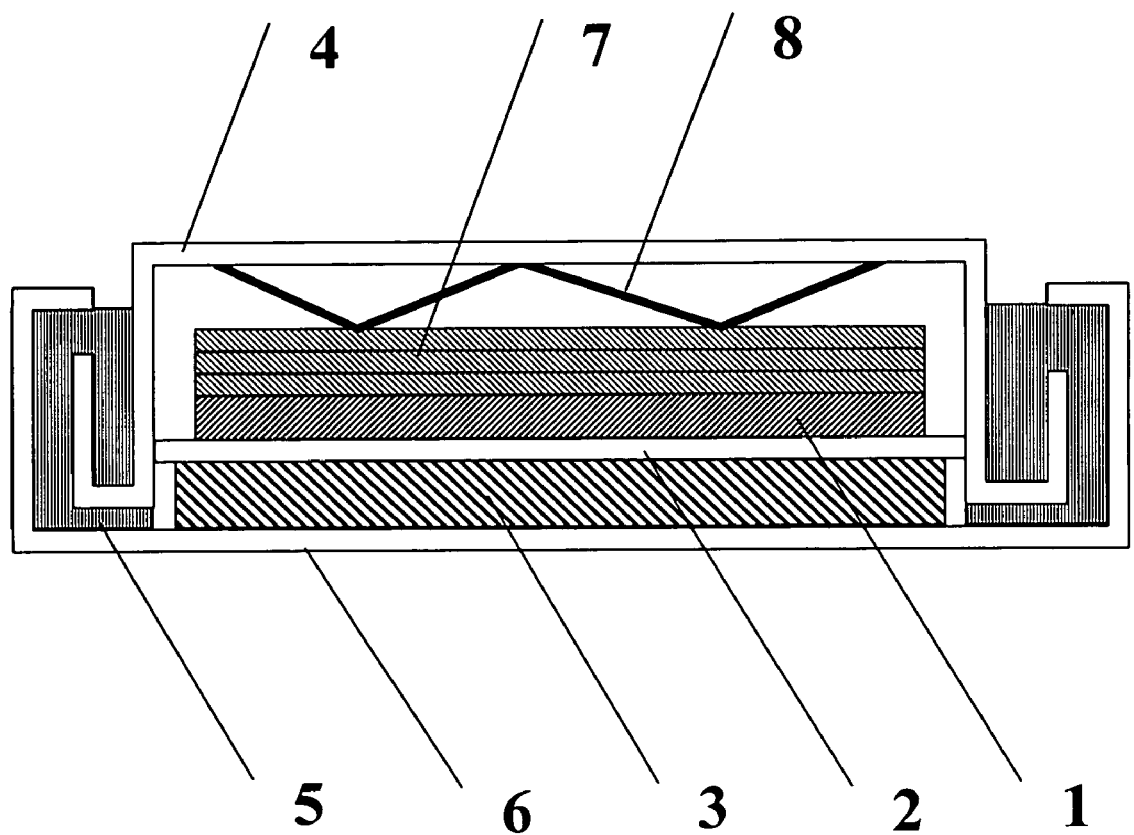
FIG. 3 is a cross section of a button cell.

A variety of 2032 type button cells were generated having a structure according to FIG. 3. The button cells include a separator 2 positioned between a cathode 1 and an anode 3. The anode and cathode are positioned in a chamber defined by a case 4, a gasket 5 and a cover 6. A spacer 7 and a spring washer 8 are positioned between the anode 3 and the case 4. The spacer 7 and spring washer 8 were made of stainless steel. An electrolyte positioned between the case 4 and the cover 6 activates the anode and the cathode. The separator was a 25 µm thick polyethylene porous membrane (Tonen Co., Ltd.).

First cathodes were generated by mixing 128.8 g of the first preliminary cathode medium from Example 1 with 58.3 g of 12 wt % solution of PVdF in n-methylpyrolidone (NMP) (Kureha Co., Ltd., PVDF1120), and 4.2 g of Carbon Black (Denka Co., Ltd.) in a mixer. The mixture was coated on a 20 µm thick aluminum foil substrate with a doctor blade. The result was dried in an oven preset at 80° C. and pressed to a 158 µm thickness. Cathodes were cut out of the result.

Second cathodes were generated by mixing 128.8 g of the second preliminary cathode medium from Example 2 with 58.3 g of 12 wt % solution of PVdF in n-methylpyrolidone (NMP) (Kureha Co., Ltd., PVDF1120), and 4.2 g of Carbon Black (Denka Co., Ltd.) in a mixer. The mixture was coated on a 20 µm thick aluminum foil substrate with a doctor blade. The result was dried in an oven preset at 80° C. and pressed to a 158 µm thickness. Cathodes were cut out of the result.

Anodes were generated by mixing 94.08 g Mesocarbon Microbeads (Osaka Gas Co., Ltd., MCMB 25-28), 40.32 g carbon fiber (Petoca, Co., Ltd., GMCF), and 100.8 g of 2 wt % carboxymethyl cellulose in water (Dai-ichi Kogyo Seiyaku Co. Ltd., Celogen WSC) and 8.4 g of 40 wt % styrene butadiene rubber (SBR) in water (Dai-ichi Kogyo Seiyaku Co. Ltd., BM-400) in a mixer. The result was coated onto a 10 µm thickness of copper foil with a doctor blade and dried in an oven preset at 80° C. The result was pressed to a 206 µm thickness. Anodes were cut out of the result.

An electrolyte was prepared by dissolving $LiPF_6$ to 1.2 M in a 25/75 by volume mixture of ethylene carbonate (EC)/diethyl carbonate (DEC).

A first cell was generated according to FIG. 3 with the electrolyte, a first cathode and an anode. A second cell was generated according to FIG. 3 with the electrolyte, a second cathode and an anode.

The cycle performance of the first cell and the second cell was measured by repeatedly charging and discharging the cells between 4.2 V and 2.7 V during subsequent cycles. The cells were discharged using constant current at a rate of 0.5 C and discharged using constant current at a rate of 0.5. The tests were carried out at room temperature.

Figure 4:
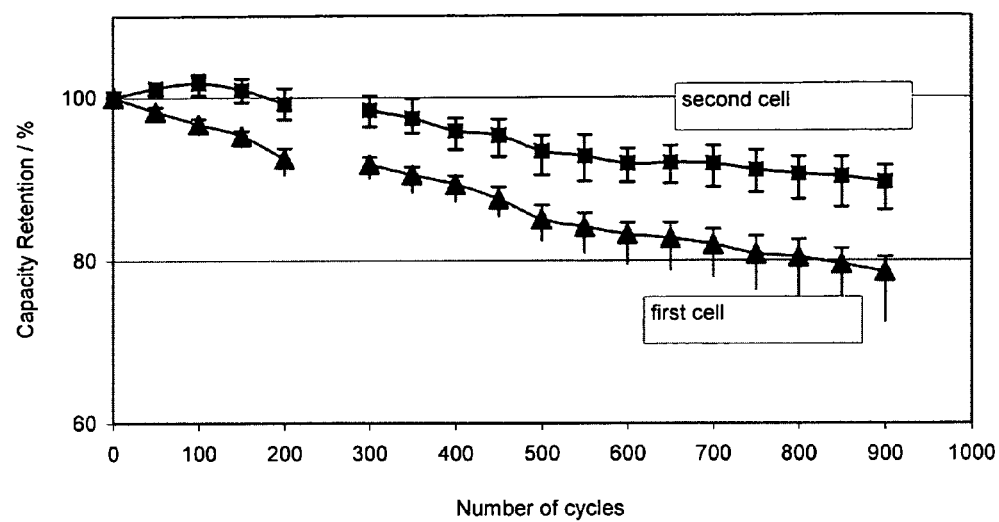
FIG. 4 compares the cycling data for a first cell having a cathode that includes the medium of FIG. 2A and a second cell having a cathode that includes the medium of FIG. 2B.

FIG. 4 presents the cycling data for the first cell and the second cell in the form of a graph showing discharge capacity retention versus cycle number. The first cell has the first preliminary cathode medium with an lithium to transition metal molar ratio of about 1.02:1.00 and the second cell has the second preliminary cathode medium with an lithium to transition metal molar ratio of about 1.05:1.00. The first cell shows a large drop in discharge capacity retention at low cycle numbers. In contrast, the second cell shows a discharge capacity retention higher than 100% at 100 cycles, higher than 98% at 200 cycles, higher than 90% at 400 cycles, higher than 86% at 600 cycles, and higher than 85% at 800 cycles.

EXAMPLE 3

A third preliminary cathode medium was generated. A mixture of Li(OH) and $Ni_{0.8}Co_{0.15}Al_{0.05}(OH)_x(NO_3)_y$ was generated with x=0.86 and y=0.14 and a lithium to transition metal molar ratio of about 1.06:1.00. The mixture was generated by the spray dry method where the Li(OH) and $Ni_{0.8}Co_{0.15}Al_{0.05}(OH)_x(NO_3)_y$ were dissolved in water and sprayed into heated air to evaporate the water. The mixture was calcinated in an oxygen atmosphere at about 720° C. so as to provide a third preliminary cathode medium that includes $LiNi_{0.8}Co_{0.15}Al_{0.05}O_2$.

A fourth preliminary cathode medium was generated. A mixture of Li(OH) and $Ni_{0.8}Co_{0.15}Al_{0.05}(OH)_x(NO_3)_y$ was generated with x=0.86 and y=0.14 and a lithium to transition metal molar ratio of about 1.08:1.00. The mixture was generated by the spray dry method where the Li(OH) and $Ni_{0.8}Co_{0.15}Al_{0.05}(OH)_x(NO_3)_y$ were dissolved in water and sprayed into heated air to evaporate the water. The mixture was calcinated in an oxygen atmosphere at about 720° C. so as to provide a fourth preliminary cathode medium that includes $LiNi_{0.8}Co_{0.15}Al_{0.05}O_2$.

Gravimetric analyses were performed on the first preliminary cathode medium, the second preliminary cathode medium, the third preliminary cathode medium, and the fourth preliminary cathode medium. The thermo gravimetric analyses were performed using a Perkin Elmer TG/TDA 6300 at a scan speed of 5° C./minute from 30° C. to 900° C. with an air flow of 200 ml/min.

Figure 5:
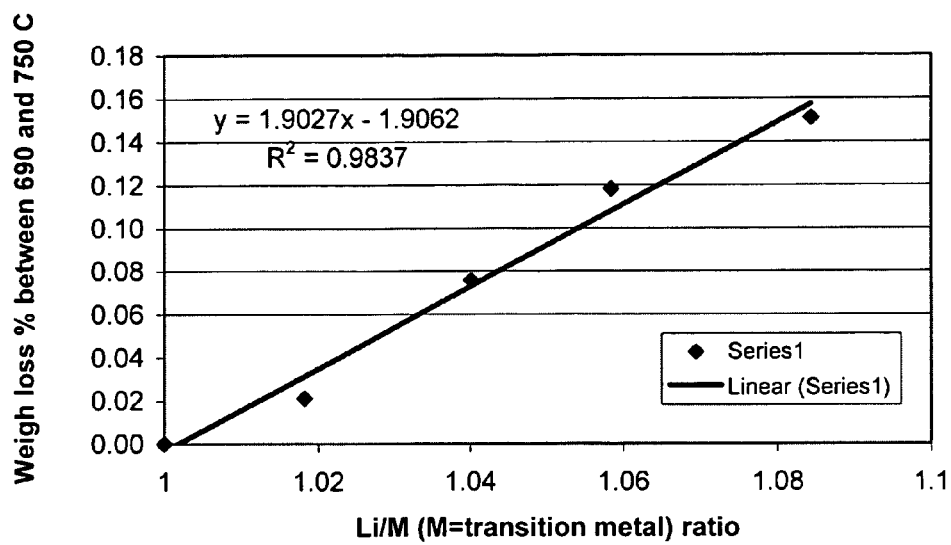
FIG. 5 illustrates an experimentally determined relationship between the percentage of weight loss in a sample of a preliminary cathode medium versus the lithium to transition metal molar ratio in the preliminary cathode medium.

Each thermo gravimetric analysis was used to determine the percentage of weight loss that occurs between 690° C. and 750° C. FIG. 5 illustrates the results of the thermo gravimetric analyses as a graph of the percentage weight loss versus the lithium to transition metal molar ratio. FIG. 5 illustrates an approximately linear relationship between the percentage weight loss versus the lithium to transition metal molar ratio. The percentage of weight loss that occurs between 690° C. and 750° C. during a thermo gravimetric analysis of other samples can be compared to the relationship illustrated in FIG. 5 to approximate the molar ratio of lithium:transition metal in the sample.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

We claim:

1. A method of forming a battery, comprising:
   generating a mixture that includes a lithium salt and a transition metal salt at a lithium:transition metal molar ratio between 1.01 and 1.09;
   calcinating the mixture so as to generate a medium that includes a lithium transition metal oxide and that includes an inactive material; and
   generating a battery having at least one cathode that includes the medium such that the lithium transition metal oxide serves as an active material.

2. The method of claim 1, wherein the inactive material includes $Li_2CO_3$.

3. The method of claim 1, further comprising:
performing a test on the medium that indicates whether a material that serves as an inactive material in a cathode is present in the medium, the test including a thermo gravimetric analysis of the medium; and
including the medium in the cathode in response to the test indicating that the inactive material is present in the medium and excluding the medium from the cathode in response to the test indicating that the inactive material is not present in the medium.

4. The method of claim 3, wherein the medium is included in the battery cathode in response to the thermal gravimetric analysis indicating that the inactive material is present in the medium and the medium is excluded from the battery cathode in response to the thermal gravimetric analysis indicating that the inactive material is not present in the medium.

5. The method of claim 3, wherein the test includes comparing results of the thermo gravimetric analysis against a relationship, the relationship being between a percentage of weight loss in a sample of a preliminary cathode medium during a thermo gravimetric analysis and a lithium to transition metal molar ratio in a preliminary cathode medium.

6. The method of claim 5, wherein comparing results of the thermo gravimetric analysis against a relationship includes approximating the lithium to transition metal molar ratio in the preliminary cathode medium.

7. The method of claim 1, wherein
the battery includes an electrolyte activating an anode and the cathode, the electrolyte including one or more salts in a solvent;
and wherein the inactive material reacts with the electrolyte to form a passivation layer that includes LiF on the cathode.

8. The method of claim 7, wherein the electrolyte preferentially reacts with the inactive material over the lithium transition metal oxide.

9. The method of claim 1, wherein the mixture is calcinated such that the lithium transition metal oxide is coated with a layer of the inactive material.

10. The method of claim 9, wherein the layer of inactive material consists of the inactive material.

11. The method of claim 10, wherein the layer of inactive material is in direct contact with the lithium transition metal oxide.

12. The method of claim 11, wherein the layer of inactive material is chemically bonded with the lithium transition metal oxide.

13. The method of claim 1, the inactive material is $Li_2CO_3$.

14. The method of claim 1, wherein the lithium transition metal oxide consists of lithium, oxygen and one or more transition metals.

15. The method of claim 14, wherein the one or more transition metals are selected from the group consisting of Li, Al, Mg, Ti, B, Ga, Si, Mn, Zn, Mo, Nb, V, Ag, Ni, and Co.

16. The method of claim 1, wherein the lithium transition metal oxide is selected from the group consisting of $LiCoO_2$, $LiNi_{1-x}Co_yAl_zO_2$, $LiNi_{1-x}Co_xO_2$, $LiNi_{1-x}Co_yMe_zO_2$, $Li_zM_yO_4$, where x' is $\geq 0$, z' is $\geq 0$, $1-x'+y'+z'=1$, $0.8<z<1.5$, $1.5<y<2.5$, M is Mn, Ti, Ni, Co, Cu, Mg, Zn, V, and combinations thereof, and Me is one or more transition metals.

17. The method of claim 9, wherein a molar ratio of the (lithium in the coated lithium transition metal oxide and in the layer):(transition metal in the coated lithium transition metal oxide and in the layer) is in a range of 1.02:1 to 1.08:1.

18. The method of claim 1, wherein the lithium:transition metal molar ratio is greater than 1.02:1.00.

19. The method of claim 18, wherein the inactive material includes $Li_2CO_3$.

20. The method of claim 18, further comprising:
performing a test on the medium that indicates whether a material that serves as an inactive material in a cathode is present in the medium, the test including a thermo gravimetric analysis of the medium; and
including the medium in the cathode in response to the test indicating that the inactive material is present in the medium and excluding the medium from the cathode in response to the test indicating that the inactive material is not present in the medium.

21. The method of claim 18, wherein the medium is included in the battery cathode in response to the thermal gravimetric analysis indicating that the inactive material is present in the medium and the medium is excluded from the battery cathode in response to the thermal gravimetric analysis indicating that the inactive material is not present in the medium.

* * * * *